(12) United States Patent  
Oldenburg et al.

(10) Patent No.: US 7,371,457 B2  
(45) Date of Patent: *May 13, 2008

(54) NANOPARTICLE COMPRISING NANOSHELL OF THICKNESS LESS THAN THE BULK ELECTRON MEAN FREE PATH OF THE SHELL MATERIAL

(75) Inventors: Steven J. Oldenburg, Houston, TX (US); Richard D. Averitt, Houston, TX (US); Nancy J. Halas, Houston, TX (US)

(73) Assignee: William Marsh Rich University, Houston, TX (US)

( * ) Notice: Subject to any disclaimer, the term of this patent is extended or adjusted under 35 U.S.C. 154(b) by 562 days.

This patent is subject to a terminal disclaimer.

(21) Appl. No.: 10/752,181

(22) Filed: Jan. 6, 2004

(65) Prior Publication Data

US 2004/0214001 A1    Oct. 28, 2004

Related U.S. Application Data

(62) Division of application No. 09/755,229, filed on Jan. 5, 2001, now Pat. No. 6,685,986, which is a division of application No. 09/038,377, filed on Mar. 11, 1998, now Pat. No. 6,344,272.

(60) Provisional application No. 60/040,570, filed on Mar. 14, 1997, provisional application No. 60/040,971, filed on Mar. 12, 1997.

(51) Int. Cl.  
*B32B 5/16* (2006.01)

(52) U.S. Cl. ............ 428/403; 977/777; 977/832; 977/835

(58) Field of Classification Search ............ 428/403; 977/773, 777, 832, 835  
See application file for complete search history.

(56) References Cited

U.S. PATENT DOCUMENTS 3,856,398 A    12/1974  Taylor .................. 355/63

(Continued)

FOREIGN PATENT DOCUMENTS

WO    WO9011890    10/1990

(Continued)

OTHER PUBLICATIONS

Howson et al., "Magnetic multilayers of Fe/Au: role of the electron mean free path", J. Phys.: Condens, Matter 11 (1999) 5717-5722.*

(Continued)

*Primary Examiner*—H. T Le  
(74) *Attorney, Agent, or Firm*—Conley Rose, P.C.; Rodney B. Carroll (57) ABSTRACT

The present invention is for particulate compositions and methods for producing them that can absorb or scatter electromagnetic radiation. The particles are homogeneous in size and are comprised of a nonconducting inner layer that is surrounded by an electrically conducting material. The ratio of the thickness of the nonconducting layer to the thickness of the outer conducting shell is determinative of the wavelength of maximum absorbance or scattering of the particle. Unique solution phase methods for synthesizing the particles involve linking clusters of the conducting atoms, ions, or molecules to the nonconducting inner layer by linear molecules. This step can be followed by growth of the metal onto the clusters to form a coherent conducting shell that encapsulates the core.

62 Claims, 6 Drawing Sheets

U.S. PATENT DOCUMENTS

| | | | | |
|---|---|---|---|---|
| 4,099,854 | A | | 7/1978 | Decker et al. ............... 350/312 |
| 4,123,396 | A | | 10/1978 | Rembaum et al. ............ 326/24 |
| 4,313,734 | A | | 2/1982 | Leuvering .................... 23/230 |
| 4,416,998 | A | | 11/1983 | Adams et al. ................ 436/86 |
| 4,452,773 | A | | 6/1984 | Molday ....................... 424/1.1 |
| 4,481,091 | A | | 11/1984 | Brus et al. ............ 204/157.1 R |
| 4,624,923 | A | | 11/1986 | Margel ....................... 435/176 |
| 4,877,647 | A | | 10/1989 | Klabunde ................... 427/123 |
| 4,979,821 | A | | 12/1990 | Schutt et al. ............... 356/246 |
| 5,023,139 | A | * | 6/1991 | Birnboim et al. ........... 428/402 |
| 5,025,147 | A | | 6/1991 | Durig et al. ................. 250/216 |
| 5,213,895 | A | | 5/1993 | Hirai et al. .................. 428/403 |
| 5,249,077 | A | | 9/1993 | Laronga et al. ............. 359/385 |
| 5,322,798 | A | | 6/1994 | Sadowski .................... 436/113 |
| 5,338,353 | A | | 8/1994 | Uchino et al. ............... 106/426 |
| 5,376,556 | A | | 12/1994 | Tarcha et al. ............... 436/525 |
| 5,451,525 | A | | 9/1995 | Shenkin et al. ............... 436/63 |
| 5,479,024 | A | | 12/1995 | Hillner et al. ........... 250/458.1 |
| 5,501,949 | A | | 3/1996 | Marshall ........................ 435/5 |
| 5,521,289 | A | | 5/1996 | Hainfeld et al. ......... 530/391.5 |
| 5,545,250 | A | | 8/1996 | Bergmann et al. ............ 75/252 |
| 5,552,086 | A | | 9/1996 | Siiman et al. ........... 252/408.1 |
| 5,567,628 | A | | 10/1996 | Tarcha et al. ............... 436/525 |
| 5,599,668 | A | | 2/1997 | Stimpson et al. .............. 435/6 |
| 5,817,462 | A | | 10/1998 | Garini et al. ................... 435/6 |
| 5,845,083 | A | | 12/1998 | Hamadani et al. ..... 395/200.61 |
| 5,938,617 | A | | 8/1999 | Vo-Dinh ..................... 600/476 |
| 6,180,415 | B1 | | 1/2001 | Svhultz et al. ............... 436/518 |
| 6,344,272 | B1 | * | 2/2002 | Oldenburg et al. ......... 428/403 |
| 6,428,811 | B1 | * | 8/2002 | West et al. .................. 424/497 |
| 6,548,168 | B1 | * | 4/2003 | Mulvaney et al. .......... 428/402 |
| 6,660,381 | B2 | * | 12/2003 | Halas et al. ................. 428/403 |
| 6,685,986 | B2 | * | 2/2004 | Oldenburg et al. ......... 427/214 |
| 6,908,496 | B2 | * | 6/2005 | Halas et al. ................... 75/370 |

FOREIGN PATENT DOCUMENTS

| | | |
|---|---|---|
| WO | WO 97/40181 | 10/1997 |

OTHER PUBLICATIONS

Scaffardi et al., "Sizing gold nanoparticles by optical extinction spectroscopy", Nanotechnology 16 (2005) 158-163.*

Birnboim, Meyer H., "Nonlinear Optical Properties of Structured Nanoparticle Composites", Mat. Res. Soc. Symp. Proc. vol. 164, 1990, pp. 277-282.

Nedelijkovic, Jovan, "Observation of Plasmon-Enhanced Optical Extinction in Silver-Coated Silver Bromide Nanoparticles", American Institute of Physics, Jun. 3, 1991, pp. 2461-2463.

Oldenburg, S.J., "Nanoengineering of Optical Resonances", Chemical Physics Letters 288 (1988), pp. 243-247.

Westcott, Sarah, "Formation and Adsorption of Clusters of Gold Nanoparticles onto Functionalized Silica Nanoparticle Surfaces", Langmuir, 1998, vol. 14, No. 19, pp. 5396-5401.

Zhou, H.S., "Controlled Synthesis and Quantum-Size Effect in Gold-Coated Nanoparticles", American Physical Society, 1994, vol. 50, No. 16, pp. 12 052-12 056.

Zhou, H.S., "Synthesis and Optical Properties of Coated Nanoparticle Composites", Journal of Luminescence, 70, 1996, pp. 21-34.

R. D. Averitt, et al; *Optical Properties and Growth Kinetics of Au coated au_2S Nanoshells*; Web Publication ; Jan. 10, 1997; (1 p.).

S. J. Oldenburg, et al; *Self-assembled Metal Shell Nanoparticles*; Web Publication; Jan. 10, 1997; (1 p.).

J. I. Steinfeld; *An Introducton to Modern Molecular Spectroscopy*; The MIT Press; Second Edition; Copyright© 1974 and 1985; (8 p.).

P. F. Bernath; *Spectra of Atoms and Molecules*; Oxford University Press 1995; (8 p.).

R. D. Averitt, et al; *Ultrafast Electron Dynamics in Gold Nanoshells*; The American Physical Society vol. 58, No. 16; 1998; (4 p.).

J. W. Haus, et al; *Nonlinear-Optical Properties of Conductive Spheroidal Particle Composites*; Optical Society of America, vol. 6, No. 4, Apr. 1989; (pp. 797-807).

D. Stroud, et al; *Decoupling Approximation for the Nonlinear-Optical Response of Composite Media*; Optical Society of America, vol. 6, No. 4, Apr. 1989; (pp. 778-786).

A. E. Neeves, et al; *Composite Structures for the Enhancement of Nonlinear-Optical Susecptibility*; Optical Society of America; vol. 6, No. 4, Apr. 1989; (pp. 787-796).

P. Barnickel, et al; *Silver Coated Latex Spheres*; Molecular Physics, 1989, vol. 67, No. 6; (pp. 1355-1372).

R. D. Averitt, et al; *Plasmon Resonance Shifts of Au-Coated $Au_2S$ Nanoshells: Insight into Multicomponent Nanoparticle Growth*; Physical Review Letters, Jun. 2, 1997, vol. 78, No. 22; (pp. 4217-4220).

D. Sarkar, et al; General Vector Basis Function Solution of Maxwell's Equations; *Physical Review*, vol. 56, No. 1, Jul. 1997; (pp. 1102-1112).

Alvarez et al., *Optical Absorption Spectra of Nanocrystal Gold Molecules*, Journal of Physical Chemistry vol. 101, No. 19, pp. 3706-3712.

* cited by examiner

NANOPARTICLE COMPRISING NANOSHELL OF THICKNESS LESS THAN THE BULK ELECTRON MEAN FREE PATH OF THE SHELL MATERIAL

CROSS-REFERENCE TO RELATED APPLICATIONS

This application relies for priority on the following two provisional applications: the first application is entitled Metal Nanoshells and is to Oldenburg et al., and was filed Mar. 12, 1997 and has serial No. 60/040,971; the second application is entitled Metal Nanoshells is to Oldenburg et al., and was filed on Mar. 14, 1997 and the serial number of that application is No. 60/040,570. These applications are specifically included herein by reference.

STATEMENT REGARDING FEDERALLY SPONSORED RESEARCH OR DEVELOPMENT

The research that resulted in this invention was funded by the Office of Naval Research, N00014-97-1-0217, and the National Science Foundation, ECS-9258118.

BACKGROUND OF THE INVENTION

It is known that solid metal nanoparticles (i.e. solid, single metal spheres of uniform composition and nanometer dimensions) possess unique optical properties. In particular, metal nanoparticles (especially the coinage metals) display a pronounced optical resonance. This so-called plasmon resonance is due to the collective coupling of the conduction electrons in the metal sphere to the incident electromagnetic field. This resonance can be dominated by absorption or scattering depending on the radius of the nanoparticle with respect to the wavelength of the incident electromagnetic radiation. Associated with this plasmon resonance is a strong local field enhancement in the interior of the metal nanoparticle. A variety of potentially useful devices can be fabricated to take advantage of these specific optical properties. For example, optical filters or chemical sensors based on surface enhanced Raman scattering (SERS) have been fabricated.

A serious practical limitation to realizing many applications of solid metal nanoparticles is the inability to position the plasmon resonance at technologically important wavelengths. For example, solid gold nanoparticles of 10 nm in diameter have a plasmon resonance centered at 520 nm. This plasmon resonance cannot be controllably shifted by more than approximately 30 nanometers by varying the particle diameter or the specific embedding medium.

Metal colloids have a variety of useful optical properties including a strong optical absorption and an extremely large and fast third-order nonlinear optical (NLO) polarizability. These optical properties are attributed to the phasic response of electrons in the metallic particles to electromagnetic fields. This collective electron excitation is known as plasmon resonance.

At resonance, dilute metal colloid solutions have the largest electronic NLO susceptibility of known substances. However, the utility of these solutions is limited because their plasmon resonance is confined to relatively narrow wavelength ranges and cannot readily be shifted. For example, silver particles 10 nm in diameter absorb light maximally at approximately 355 nm, while similar sized gold particles absorb maximally at about 520 nm. These absorbance maximums are insensitive to changes in particle size and various dielectric coatings on the particles.

One method of overcoming this problem is to coat small nonconducting particles with these metals. For example, the reduction of Au on $Au_2S$ (reduction of chloroauric acid with sodium sulfide) particles has been shown to red shift the gold colloid absorption maximum from 520 nm to between approximately 600 nm and 900 nm, depending on the amount of gold deposited on the $Au_2S$ core and the size of the core. Zhou, et al. (1994). The ratio of the core radius to shell thickness can be controlled by changing the reactant concentrations or by stopping the reaction. In this case, the diameter of the particle core is directly proportional to the red shift in the wavelength of light that induces gold plasmon resonance. However, gold-sulfide particle diameters are limited to sizes of approximately 40-45 nm with a thin gold shell (less than 5 nm). The limited size of the gold-sulfide particles of Zhou et al. limits the absorbance maximum to wavelengths no larger than 900 nm. See, also Averitt et al. (1997) An additional limitation of such particles as defined by Zhou et al. is that both the core and the shell are grown as a result of a single chemical reaction, thus limiting the choice of the core material and the shell material to $Au_2S$ and Au respectively. In addition, only the ratio of the core radius to shell thickness may be controlled; independent control of the core radius and the shell thickness is not possible.

Neideljkovic and Patel (1991) disclosed silver-coated silver bromide particles that are produced by intense UV irradiation of a mixture of silver bromide, silver, sodium dodecylsulfate (SDS) and ethylenediamine tetraacetic acid (EDTA). The Neideljkovic particles range in size from approximately 10 to 40 nm and are irregularly-shaped, as determined by transmission electron micrography. Predictably, the spectra obtained from these particle preparations are extremely broad.

In U.S. Pat. No. 5,023,139, Bimboim et al. disclosed theoretical calculations indicating that metal-coated, semiconducting, nanometer-sized particles containing should exhibit third-order nonlinear optical susceptibility relative to uncoated dielectric nanoparticles (due to local field enhancement). Their static calculations were based on hypothetical compositions. The preferred embodiments disclosed by Birnboim et al. are, in fact, not particles with metallic shells on their surfaces. In those embodiments theoretically proposed by Bimboim et al. that do in fact propose a metal outer shell, there is an additional requirement as to the specific medium in which they must be used in order to properly function.

However, Bimboim does not disclose methods for preparing the disclosed hypothetical compositions. Furthermore, Birnboim's calculations do not take into account surface electron scattering. Surface electron scattering strongly modifies the optical response of all metallic structures that possess at least one dimension smaller than the bulk electron mean free path (e.g. in Au at room temperature the bulk electron mean free path is about 40 nm). This effect reduces the local field enhancement factor that in turn reduces the resonant third order nonlinear optical susceptibility associated with the nanoshell geometry. See, Averitt et al. (1997). Since typical shell thicknesses for these compositions fall below 40 nm, Birnboim et al's theoretical calculations fail to account for this effect which is an important aspect of the optical response for functional metal nanoshells. Finally, it is important to realize that the hypothetical metal nanoshells of Bimboim pertains specifically to the enhancement of the third order nonlinear optical susceptibility.

Moreover, Birnboim-type particles are by definition particles much smaller than a wavelength of light (less than 0.10 times a given wavelength of light), and are particles in which the dielectric property of the nanoshell (in those instances where it is in fact a metal shell that is used in Bimboim et al.) are defined as the bulk dielectric property of the metal selected. In practice, this requires these smaller-than-a-wavelength particles to have metal shell layer thicknesses of many nanometers (e.g., for Au, such minute particles meeting the theoretical requirements of the Birnboim calculations and the bulk dielectric properties of Au required thereby, would necessarily have shells at least 40 nm in thickness). The physical limitations placed on the construction of such particles is therefore considerable.

Methods and materials are needed that can be used to shift the wavelength of maximum absorption of metal colloids. Methods for producing materials having defined wavelength absorbance maxima across the visible and infrared range of the electromagnetic spectrum are needed Particularly, such metal nanoshell composites should be constructed in a manner to allow a choice of core material, core dimensions, and core geometry independent of those criteria for the shell material. Compositions produced by these methods should have relatively homogeneous structures and should not have to rely on suspension in a particular medium in order to exhibit their desired absorption characteristics. Moreover, materials and methods are needed that are not limited in the radial dimensions of the shell layer by the bulk dielectric properties of the metal selected, and are not limited in size to much smaller than a wavelength of light. Materials impregnated with these compositions could be used in such diverse applications as optical switching devices, optical communication systems, infrared detectors, infrared cloaking devices, passive solar radiation collection or deflecting devices and the like.

BRIEF SUMMARY OF THE INVENTION

The present invention relates to compositions and methods for synthesizing unique composite particles having homogeneous structures and defined wavelength absorbance maxima. The present compositions consist of a nonconducting inner layer that is surrounded by a layer made of a conducting material. Also contemplated are unique methods for making the present compositions such that the resulting compositions can be tuned to absorb electromagnetic radiation maximally at wavelengths in the visible or infrared regions of the electromagnetic spectrum.

Particularly, the metal nanoshells of the present invention are not restricted to a single core or single shell material; permutations of materials are made possible by the novel methodology disclosed here for the first time to make such metal nanoshells. There is no requirement to use the metal nanoshells of the present invention in any given medium in order for them to exhibit their absorptive qualities; in fact, it is anticipated that such metal nanoshells may find particular utility as surface treatments and coatings totally absent any surrounding medium. Because the core and shell material is selected independently, any number of such permutations is made possible. The particles of the invention are also relatively uniform in size and shape by virtue of the methods of the invention used to construct them. Most importantly, while the metal nanoshells of the present invention may be much smaller than a wavelength of light, they are not limited in the thickness of their metal shells to account for the bulk dielectric properties of the metal comprising the shell. In fact, due to the one-atom-or-molecule-at-a-time approach to building the metal shell disclosed by the present inventors, the thickness of the metal shell may be controlled from as low as atomic thicknesses.

The spectral location of the maximum of the plasmon resonance peak for this geometry depends sensitively upon the ratio of the core radius to shell thickness, as well as the dielectric functions of the core and shell. The presence of a dielectric core shifts the plasmon resonance to longer wavelengths relative to a solid nanoparticle made exclusively of the metallic shell material. For a given core radius, a thin shell will have a plasmon peak that is shifted to longer wavelengths relative to a thicker shell. It is to be emphasized that metal nanoshells possess all of the same technologically viable optical properties as solid metal nanoparticles in addition to this extremely important aspect of resonance tunability.

This invention relates in certain regards to a general method for the production of nanoshell composites. In particular, the choice of the core material and geometry can be determined independently of the shell material. Similarly, the choice of the shell material and shell thickness is independent of the desired core material. It is also important to note that the coating methods and materials described herein will allow for the fabrication of other unique geometries with potentially unique properties; the utility of this method extends far beyond the fabrication of spherical nanoshells. For example, coated cubes or pyramids or cylinders, planar surfaces, or structures patterned onto or etched into a planar surface, to name a few, can be easily fabricated using the same methods detailed herein.

Figure 1:
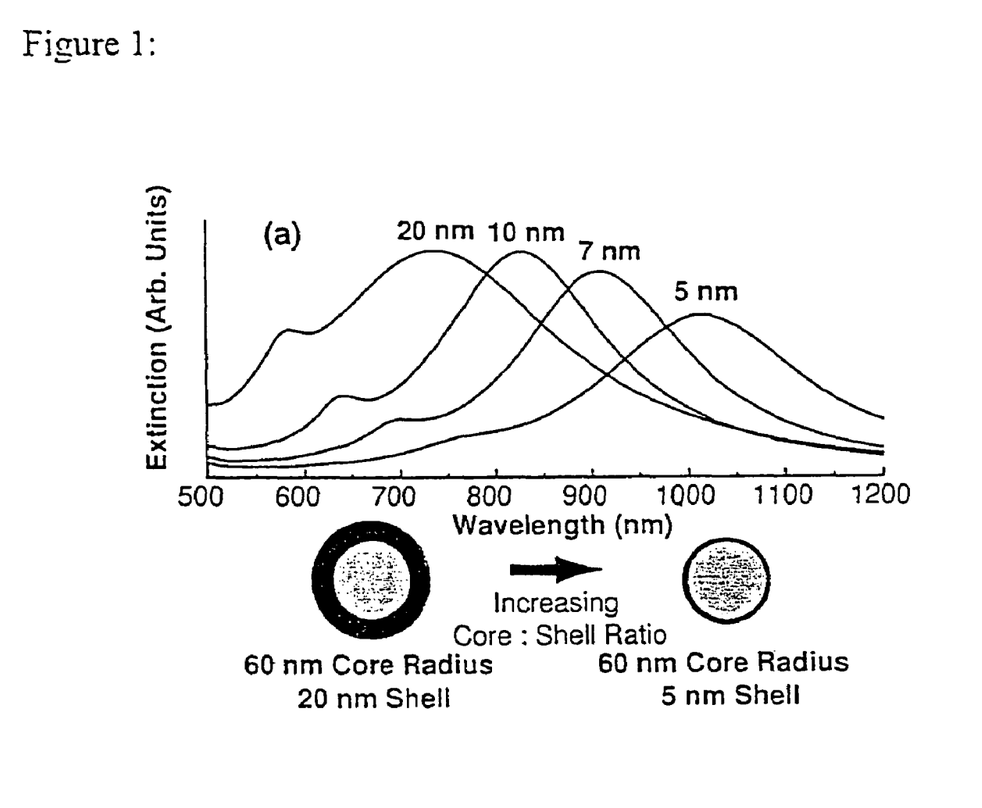
FIG. 1: Calculated optical resonances of metal nanoshells (silica core with gold shell in water) over a range of core radius/shell thickness ratios.

The present embodiments have wavelength absorbance maxima in the range of approximately 400 nm to 20 μm. The low wavelength end of the range is defined by the natural plasmon resonance of the metal-like conductor in a shell layer. For any given particle, the maximum absorbance depends upon the ratio of the thickness of the nonconducting layer to the conducting shell layer. Shown in FIG. 1 are absorption maxima for particles having core to shell ratios of 60:20, 60:10, 60:7, and 60:5. As shown, these particles have absorbance peaks of approximately 740, 830, 910, and 1010, nanometers respectively.

The specially tailored particles or particle mixtures of the invention can be added to polymers during their preparation by methods well known in the art. Suitable polymers include polyethylene, polyvinyl alcohol (PVA), latex, nylon, teflon, acrylic, kevlar, epoxy, glasses and the like. Solubility of nanoparticles into polymers can be facilitated by functionalization of the nanoparticle surfaces with suitable molecules known to those of skill in the art. The resulting coatings and materials can absorb radiation over the wavelength region of the incorporated particles. Embodiments containing these materials can be used in thermal management to produce more energy efficient buildings, automobiles and storage chambers creating savings in air conditioning and heating costs. Fullerene and/or polymer thin film chemistry could be used to incorporate the present materials into photovoltaic devices by methods known in that art. This approach extends the spectral response of solar cells across the infrared region of the solar emission spectrum, providing more efficient solar cells. Similarly, solar cells or similar devices operated in a photoconductive rather than photovoltaic mode could be used to provide new low-cost, compact infrared detectors useful for a range of applications, including but not limited to environmental emissions testing, medical imaging or night vision surveillance.

The compositions of the present invention are particles that have at least two layers. At least one layer is immediately adjacent to and surrounds another layer. The innermost layer is said to be a core. A layer that surrounds the core is said to be a shell layer. The shell layer is metal-like in that it can conduct electricity and is made of a metal or metal-like material. It is preferred that at least one shell layer readily conduct electricity, however, the invention only requires that one shell layer have a lower dielectric constant than the adjacent inner layer. In some embodiments, this metal or metal-like shell layer is the outermost layer. In other embodiments, the shell layer immediately adjacent the core is not the outer most shell layer. Additional layers, such as a non-conducting layer, a conducting layer, or a sequence of such layers, such as an alternating sequence of non-conducting and conducting layers, may be bound to this shell layer using the methods described herein and using materials and methods known well to those of skill in the relevant art. Thus, for the purposes of this invention the term conductor is defined by reference to the adjacent inner layer and includes any material having a lower dielectric constant than its immediately adjacent inner layer.

It is also preferred that the adjacent inner layer to the shell layer be nonconducting. Specifically contemplated are nonconducting layers made of dielectric materials and semiconductors. Suitable dielectric materials include but are not limited to silicon dioxide, titanium dioxide, polymethyl methacrylate (PMMA), polystyrene, gold sulfide and macromolecules such as dendrimers. In certain embodiments of this invention, the nonconducting layer is comprised of a semiconductor material. For example, core particles may be made of CdSe, CdS or GaAs. The material of the nonconducting layer influences the properties of the particle. For example, if the dielectric constant of the shell layer is larger relative to a particle having a core with a given dielectric constant, the absorbance maximum of the particle will be blue-shifted relative to a particle having a core with a lower dielectric constant. The core may also be a combination or a layered combination of dielectric materials such as those listed above.

One layer of a particle is its core as noted above. In a two layer particle, the core is a nonconducting layer. The preferred core is a monodisperse, spherical particle that is easily synthesized in a wide range of sizes, and has a surface that can be chemically derivatized. It is also preferred that cores be made of dielectric materials or semiconductors.

Although in preferred embodiments the core is spherical in shape, the core may have other shapes such as cubical, cylindrical or hemispherical. Regardless of the geometry of the core, it is preferred that the particles be homogenous in size and shape in preferred embodiments. In other embodiments, mixtures are purposefully constructed wherein there is a controlled size and shape distribution. In spherical embodiments, particles have a homogeneous radius that can range from approximately 1 to 10 nanometers to several microns depending upon the desired absorbance maximum of the embodiment. For the purposes of this invention, homogeneity exists when over about 99% of the particles do not vary in diameter by more than 100%. Under this definition a particle preparation wherein 99% of the particles have diameters between about 50 nm to 100 nm would be said to be homogeneous. Specific applications, however, as discussed in the examples, may rely on mixtures of metal nanoshells with different core and shell sizes.

Monodisperse colloidal silica is the preferred nonconducting layer or core material. These particles can be produced by the base catalyzed reaction of tetraalkoxysilanes, by techniques known well to those of skill in the art. Nearly spherical silica cores having sizes ranging from 10 nm to greater than 4 µm with a variation in particle diameter of only a few percent are preferred.

In the present embodiments, at least one nonconducting layer is surrounded by a layer that is made of a conducting material. Generally, the conducting layer is metallic but it may also be an organic conducting material such as polyacetlene, doped polyanaline and the like. Suitable metals include the noble and coinage metals but any metal that can conduct electricity is suitable. Metals that are particularly well suited for use in shells include but are not limited to gold, silver. copper, platinum, palladium, lead, iron or the like. Gold and silver are preferred. Alloys or non-homogenous mixtures of such metals may also be used.

The conducting shell layers of the present invention have thicknesses that range from approximately 1 to 100 nm. They may coat the adjacent inner layer fully and uniformly or may partially coat that layer with atomic or molecular clusters. In either embodiment, at least approximately 30% of the adjacent inner layer is coated by the conducting layer.

In certain embodiments, the shell layer is linked to the dielectric core layer through a linker molecule. Suitable linker molecules include any molecule that is capable of binding both the core and atoms, ions or molecules of the shell. Preferably, linker binding is covalent to both the shell and the inner layer but binding may also be through ionic bonds, lone-pair interactions, hydrogen bonds, Van der Waals interaction or the like. In certain embodiments, the linker binds existing metallic clusters to the surface of a non-conducting layer. In other embodiments, the linker binds atoms, ions or molecules directly to the surface of a non-conducting layer. Thus, in embodiments that have a core made of CdSe, a suitable linker would be able to bind the CdSe core and molecules in the shell. In preferred embodiments, the silicone dioxide core and gold metallic shell, are linked by aminopropyltriethoxy silane ("APTES").

The present invention also contemplates unique chemical methods for producing the disclosed compositions in solution. Generally, assembly occurs by way of the following steps. First, core particles are grown or otherwise obtained. Next, a linker molecule is bound to the core. Then, clusters of molecules that comprise the conducting shell layer are reacted with a free reactive end on the linker molecules. These clusters may complete the shell layer or form nucleation sites for the growth of a complete shell layer around the core.

The conditions under which each of the synthetic reactions is carried out determines the overall size and makeup of the particle. For example, in the synthesis of metal shells, reactants include certain concentrations of metal and reducing equivalents that can be altered along with reaction times to vary the shell thickness and morphology. With certain shell materials, the progress of this reaction can be followed spectrophotometrically due to the distinct absorption peaks of the particles in the visible and infrared regions of the electromagnetic spectrum.

One method for obtaining core particles is by the synthetic method described in Example II, which can be used to synthesize particles of silicon dioxide. Alternatively, in some cases suitable core particles may be purchased. For example, silicone dioxide core particles such as LUDOX TM-50 colloidal silica are available from Aldrich Chemical Co., Milwaukee, Wis.

One unique aspect of the present method is the attachment of conducting materials of the shell to the nonconducting inner layer. In the methods of the invention, this step is carried out in solution. In this method, linker molecules that are capable of chemically linking the conducting layer to the core are first bound to the core. One method of attachment, described in Example III, is for the reaction of APTES with silicon dioxide particles. Other suitable linker molecules include but are not limited to mercaptopropyltrimethoxy silane, 4-aminobutyldimethoxysilane, and the like. One of skill in the art will readily appreciate that the suitability of a linker molecule depends upon the particular embodiment including the composition of the core and of the conducting shell that will eventually surround the core. With this knowledge, one of skill can identify suitable linkers and bind them to core particles or nonconducting inner layers and then react suitable conducting molecular clusters, ions, or atoms of a suitable conducting material to them.

As one of skill in the art can readily appreciate, suitable solvents for linker molecule attachment depend upon the reactants and a variety of solvents may work under a given set of conditions. In Example III, the solvent of choice for the attachment of APTES to silicon dioxide is anhydrous ethanol. Generally, where linkers are attached in condensation reactions, the preferred solvents are anhydrous because such solvents tend to drive the reactions to produce more of the desired final reacted product. One of skill in the art would be able to select a suitable solvent based on chemical methodologies well known in the chemical arts.

Once the linker molecules are bound to the core, a free reactive moiety on the linker is reacted with clusters of molecules, ions or atoms to produce all or part of a conducting shell. In certain embodiments, the clusters are metal atoms. When the clusters are metallic, one suitable attachment method is disclosed in Example IV. Metal clusters, ions or atoms that are linked to the core particle through a linker molecule are said to be "tethered." In certain embodiments the tethered metal atoms or clusters serve as nucleation sites for the deposition of additional metal from solution. In other embodiments, the attachment of metal clusters completes the synthesis.

Methods for the growth of a complete metallic shell on tethered metal clusters are disclosed in Example V. Generally, metal is deposited onto the tethered clusters and enlarges the clusters until a coherent metal shell of the desired thickness is formed. In the method of Example V, the metal can be deposited through reduction process of solution metal onto the tethered clusters. Alternatively, metal can be deposited on the tethered metal clusters by a "colloid-based" deposition process. The deposition can also be initiated or driven photochemically. The technique of depositing metal onto metal nucleation sites tethered to nonconducting core materials in solution is one of the novel features of the present methods.

In certain preferred embodiments, the metallic shell is the terminal layer. However, attachment of molecules or additional layers can change the physical properties of the particle. A chemical or charge-transfer interaction between the metallic shell and an additional layer, or just the local embedding medium, influences the optical absorption of the particles, as discussed by Kreibig et al, incorporated herein by reference to the extent it provides such methods.

In addition, the near field of the metallic shell can affect the properties of molecules adsorbed on the surface of the nanoparticles. This could be of use in chemical sensing applications. In other embodiments, a non-conducting layer surrounding the metallic layer can provide a steric barrier that is useful when processing or organizing the particles into a particular arrangement. Chemical functionalization of the metal surface is also useful for transferring the metal nanoshells between different solvents, as discussed by Sarathy et al., incorporated herein by reference to the extent it provides such methods. Chemical functionalization may also assist or enable the formation of arrays or crystals of these particles, which will possess additional unique optical properties relating to the periodicity of the array or crystal structure, in similarity with photonic band gap crystals and arrays.

Figure 2:
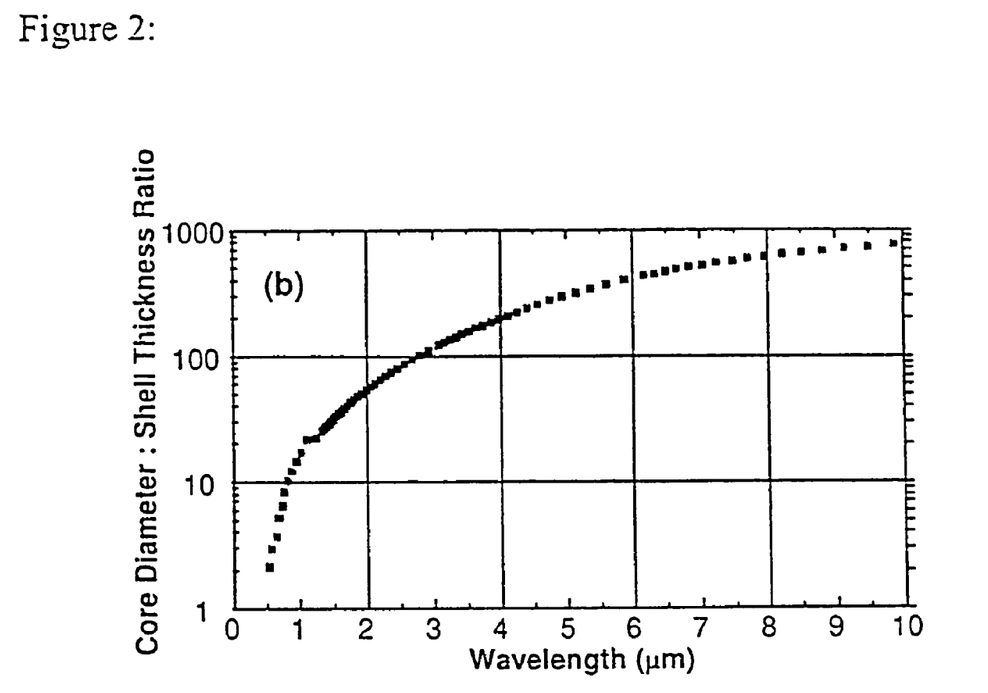
FIG. 2: Calculation of optical resonance wavelength versus core radius/shell thickness ratio for metal nanoshells (silica core with gold shell in water).

By varying the conditions of the metal deposition reaction, the ratio of the thickness of the metal shell to the nonconducting inner layer can be varied in a predictable and controlled way. Particles can be constructed with metallic shell layer to core layer radius with ratios from 10 to $10^{-3}$. This large ratio range coupled with control over the core size results in a particle that has a large, frequency-agile absorbance over most of the visible and infrared regions of the spectrum. A theoretical calculation of the plasmon resonance as a function of core/shell ratio is shown in FIG. 2.

There are many possible applications of metal-coated nanoparticles that could utilize the tunability of the plasmon resonance. Nanoshells could be made to absorb or scatter light at specific wavelengths in the visible or infrared range. Such compositions would be ideal for use in a wide range of materials including energy efficient paints, windows, coatings, or fabrics that could be used on or in vehicles and building structures. These compositions could be suspended as an active agent in inks, for cryptographic marking purposes. These materials would also be particularly well suited for use in air heating units or in solar collector materials. Such a solar absorber could also be used as a shield or screen that absorbs or scatters incident solar radiation, keeping the structure cooler than if it were directly exposed to the solar radiation.

Such materials could be useful in many other applications to efficiently "manage" the radiation from any thermal source. For example, these compositions could be adsorbed onto or embedded into materials, thin films, coatings, or fabrics that convert radiation directly into heat (passive solar energy harvesting), or into devices or device components, that convert radiation into electricity via photovoltaic or photoconductive effects, or that convert radiation into chemical energy (fuel cells). Mixtures of these compositions could be made to absorb or scatter solar energy across the entire solar radiation spectrum.

These nanoparticles could be used to sensitize existing photovoltaic, photoconductive, or bolometric devices for enhanced photoresponse and efficiency, and could be used as the functional basis for new device designs. The strong infrared photoresponse of these compositions may be useful for sensitization of many different types of semiconductor or polymer surfaces or films for other applications.

For example, the selective infrared absorption may be useful for laser eye protection, or eye protection from other potentially damaging sources of infrared radiation. The enhanced optical field in the vicinity (1-20 nm) of a nanoparticle may facilitate photochemistry or photoelectrochemistry, either on a nanoparticle surface, on a substrate upon which a nanoparticle is attached, or an electrode upon which the nanoparticle is attached or embedded. Structures containing such compositions could be used in photoconductive applications such as in infrared detectors. Infrared detectors utilizing the properties of these compositions could be used in a wide range of applications such as detecting emissions in environmental monitoring, optical telecommunications networks, wavelength selective, mid-infrared detectors for medical imaging, night vision surveillance equipment or infrared telescopes.

Compositions constructed with different resonant frequencies could be selectively manipulated, levitated, or "sifted" using the wavelength dependent dipole force of a laser beam or beams. Additionally, metal nanoshells can be made that possess unique electronic properties that could be useful in specific electronic device applications. The fabrication of homogeneous metal shells comprised of several hundred or a few thousand atoms covering dielectric cores as small as 1 nm would have well-defined electronic energy levels, similar to molecules, whose energy level spacings are controllably defined by the nanoshell geometry as described by Puska and Neiminen, incorporated herein by reference to the extent it provides such methods.

In other words, the energy eigenstates of very small diameter metal nanoshells are defined not only by the shell thickness, but by the diameter of the inner core as well. For small core diameters, both the optical and electronic properties are unique to the ultra small core/shell structure. Such metal nanoshells might find application in nanoscale devices, such as single electron transistors or coulomb blockade devices that rely on having well defined electronic energy level spacings. They may also provide useful electronic or electrical properties as components of larger devices. In addition, there could be higher energy optical resonances of metal nanoshells that lie in the vacuum ultraviolet or x-ray region of the electromagnetic spectrum, a property that could be applied to the fabrication of x-ray absorbers or detectors.

The enhanced polarizability at the plasmon resonance of these compositions could be used in chemical sensing or chemical analysis applications, where information concerning the properties of molecules adsorbed onto the nanoparticle surface is obtained. Such compositions may permit the use of surface enhanced raman scattering (SERS) to be performed upon adsorbate or adjacent molecules using laser wavelengths in the near-infrared or infrared region of the spectrum. For compositions prepared where the shell is incomplete, second-order nonlinear optical effects may be enhanced when such oriented compositions are adsorbed onto a surface or embedded into an appropriate medium.

DETAILED DESCRIPTION OF THE INVENTION

The following examples are offered by way of illustration and are not intended to limit the invention in any manner. In the examples all temperatures are in degrees Celsius and all percentages are by weight for solids and volume if for liquids unless otherwise noted.

EXAMPLE I

General Method for Metal Nanoshell Colloid Based Synthesis

Versatile methods for the synthesis of nanoparticle cores and metal shells of defined sizes have been developed and are described below. Generally, the method comprised the following steps:

(1) first a dielectric or semiconductor nanoparticle core was obtained and dispersed in solution;
(2) then 1-2 nm metal-like "seed" colloids were attached to the surface of the nanoparticle core via molecular linkages, covering the core surface with a discontinuous metal colloid layer;
(3) finally, additional metal was deposited onto the metal-like adsorbates by a solution phase chemical reduction reaction.

This nanoparticle assembly method was carried out with silica nanoparticles and gold colloid. Both commercially available silica nanoparticles and silica nanoparticles grown in situ were used successfully. The organosilane linkage molecule 4-aminopropyltriethoxy silane was absorbed onto the nanoparticle core. Gold colloid was then introduced into a solution containing the core particles. The gold colloidal nanoparticles bound to the organosilane linker molecules and covered the silica cores with a discontinuous layer of metal clusters. Subsequently, gold metal atoms were deposited onto the tethered metal clusters by reduction from solution.

EXAMPLE II

Core Particle Synthesis

Initially a core material for the nanoparticle was prepared. This material had a spherical shape, and was approximately uniform in size. The silica particles produced in the following procedure had a standard deviation of less than 10% (4% is routinely achievable).

The method of Stober (1968), incorporated herein by reference to the extent it provides such methods, was used to produce monodisperse silicon dioxide particle cores. Tetraethyl orthosilicate (TEOS) 99.999% was obtained from Aldrich Chemical Co., sodium hydroxide was from Fluka Chemical Co. and highly purified water was obtained from a Millipore "TOTALQ" system that included "MILLIQ$^{UV}$" and "MILIQ$^{RO}$" filters. All glassware was cleaned with chromic acid solution and thoroughly rinsed with "TOTALQ" water.

Variations in water, base concentration, and TEOS concentration were used to produce monodisperse silica spheres of various sizes. Temperature and electrolyte concentration also affected the final diameter of the particles. Generally, the following concentration ranges were used: 0.1 to 0.5 M TEOS, 0.5 to 17 M $H_2O$, and 0.5 to 3.0 M ammonia. In addition, a variety of alcohols were used as solvents, however, ethanol was preferred. Higher ammonia concentrations provide larger particles.

Uniform particles having a diameter of 120 nm as measured by a transmission electron microscope (TEM) were prepared by the following method. Approximately 50 milliliters (ml) of dry (100%) ethanol and 4 ml of $NH_4OH$ (25% $NH_3$ in water), were stirred in a glass beaker. To this solution, 2.2 ml of tetraethyl orthosilicate having a purity of at least 99.999% was added and allowed to stir for at least 8 hours. By varying the concentrations of $NH_4OH$, water and silicate among other factors, the size of the silica particle was varied from approximately 20 nm to 500 nm diameter. Larger core particles were grown using a seeded growth technique where additional TEOS and water were added to already formed silica particles. Multiple additions of small amounts of additional reactants allowed monodisperse core particles to be grown as large as 4 microns.

EXAMPLE III

Linker Molecule Attachment

To assemble a metallic shell around an inner layer frequently required the use of linker molecules. These molecules were chemically linked to the inner layer and served to bind atoms, ions, atomic or molecular clusters of the conducting shell to the inner layer. The conducting shell atoms that bound to the linkers were used as nucleation sites for reduction of the additional atoms or molecules to complete the shell. One method used to attach gold particles to silicon dioxide was to treat the particles with aminopropyltriethoxy silane (APTES). The silanol end groups of the APTES molecules attach covalently to the silica core extending their amine groups outward as a new termination of the particle surface.

In this method, 10 ml of a silica particle suspension such as prepared in Example III, was added to a 50 ml glass beaker. Next, pure aminopropyltriethoxy silane (APTES) was added to the solution. Based on estimates enough silane was added to coat the particles with multiple layers of silane. For example, 40 microliters of undiluted APTES was used for particles having diameters of 120 nm. The solution was stirred for 2 hours, diluted to 200 mls and then heated to a boil for four hours. The heating step promotes the reaction of silanol groups into Si—O—Si bonds and strengthens the attachment of the silane to the silica. This mixture was centrifuged at 2000×g for 30 minutes. The supernatant was decanted off and the pellet was redispersed ultrasonically. This washing procedure was repeated five times.

Many linker molecules other than aminopropyl triethoxy silane are suitable for use in this procedure. For example, aminopropyl trimethoxy silane, diaminopropyl diethoxy silane, or 4-aminobutyl dimethylmethoxysilane and the like can be used. In addition, the surface can be terminated with a linker that allows for the direct reduction of metal atoms on the surface rather than through a metallic cluster intermediary. In other embodiments, reaction of tetrahydrothiophene(AuCl) with a silica core coated with diphenyltriethoxy silane leaves a surface terminated with gold chloride ions which can provide sites for additional gold reduction. In other embodiments, a thin shell of another nonmetallic material, such as CdS or CdSe grown on the exterior of a silica particle allows for a metallic shell to be reduced directly onto the nanoparticle's surface. In other embodiments, functionalized oligomers of conducting polymers can be attached in solution to the functionalized or nonfunctionalized surface of the core nanoparticle and subsequently cross-linked by thermal or photo-induced chemical methods.

EXAMPLE IV

Attachment of Metal Clusters

Metal clusters were attached to the linker molecules on the core by immersing the derivatized core particles in a metal colloid bath. Any metal that can be made in colloidal form could be attached as a metal cluster. For example, silver, platinum, palladium, lead and the like could be used. In addition, metal-like organic molecules are suitable. Such compounds include polyacetlene and polyaniline. Gold clusters having a diameter of 1-3 nm were grown using the reduction reaction as described by Duff, incorporated herein by reference to the extent such methods are disclosed. A solution of 45 ml of water, 300 microliters of 1 M NaOH and 1 mL of a freshly diluted 1% aqueous solution of tetrakis (hydroxymethyl)phosphonium chloride (THPC) was stirred in a 100 ml flat bottom beaker with a pyrex coated magnetic stir bar. After 2 minutes, 2 ml of chloroauric acid (25 mM dark-aged stock solution, hydrogen tetrachloroaurate (III) trihydrate 99.999% from Aldrich) was added. This reaction mix was used to form gold particles in solution with an average particle diameter of 1-2 nm. To increase the size of the particles higher concentrations of gold chloride could be used. Particles prepared in this fashion were referred to as ultra small gold particles or (UG).

Generally, the UG solution was mixed with silica particles in an amount that would theoretically cover the core particle surface five to ten times. The solution was allowed to react for 3 hours under gentle stirring. In the preferred embodiment the gold was used 5-30 days after it was made.

Typically, after three hours, unreacted gold colloid was separated from the gold-decorated silica particles by centrifugation at 1000 RCF. The minimum amount of centrifugal force required to effect separation was used to avoid coalescence of the particles. Particles were washed twice by resuspension and centrifugation.

The inventors made the surprising discovery that the gold decorated particles did not aggregate after being centrifuged and redispersed in the absence of additional stabilizing compounds. This discovery allowed the convenient separation of the decorated silica from colloidal gold, leaving the gold attached to silica in a chemically reactive state. Various protectants could be added before centrifugation to facilitate later resuspension of the particles. These protectants include polyvinyl alcohol, polyethylene glycol or phosphine ligands, and thiol-terminated carboxylic acid linkages. Resuspension was easily accomplished when a minimum amount of force was used in the centrifugation step and any aggregates of particles could be redispersed by treatment with sonification. A dynamic light scattering instrument was used according to standard and well known methods to verify that the particles were dispersed. The dispersed particles were diluted to 10 mls and used as a stock solution for the growth of the complete metal shell.

EXAMPLE V

Growth of the Shell

The metal clusters were enlarged by deposition of gold using a variety of reductants such as hydroxylamine hydrocholoride, sodium borohydride, and formaldehyde. Formaldehyde was preferred. A solution of 25 mg anhydrous potassium carbonate was added to 100 ml of water containing 1.5 ml of 25 mM chloroauric acid solution (PCG). This solution was allowed to age in the dark for one day. Approximately 10 ml+/−5 ml of PCG was rapidly stirred with 2-5 mls of the gold clustered silica solution. A 100 microliter aliquot of freshly prepared formaldehyde solution (2% by volume in water) was slowly added.

Figure 3:
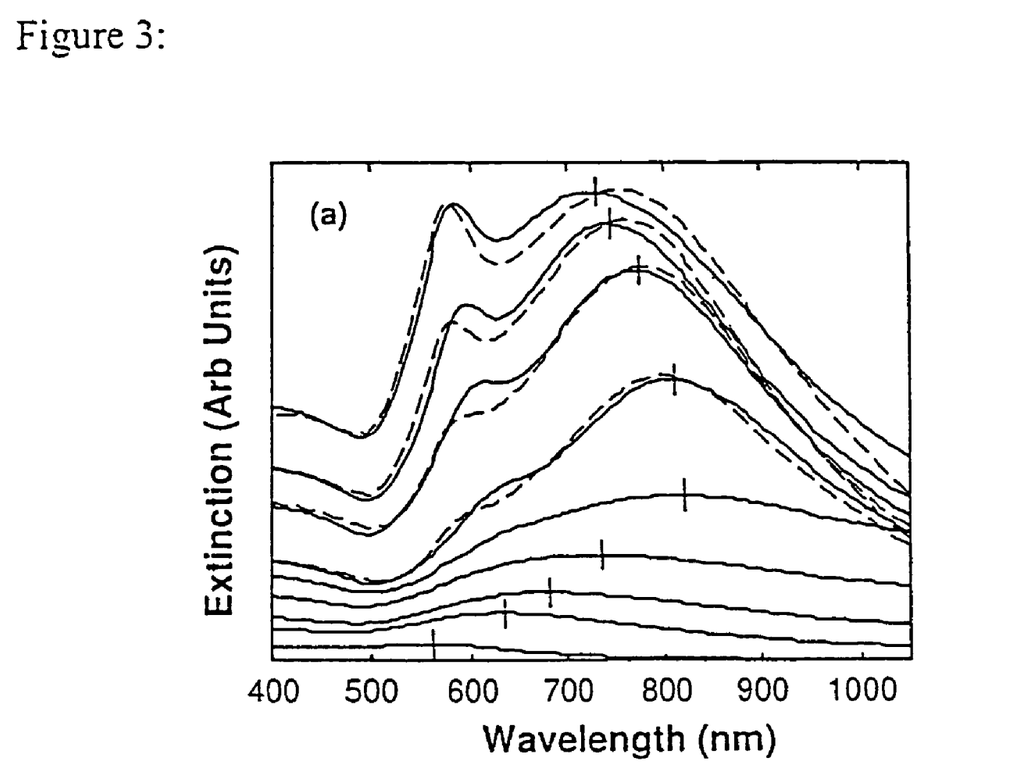
FIG. 3: Growth of gold shell on 120 nm diameter silica core particles. The lower spectral curves follow the evolution of the optical absorption as coalescence of the gold layer progresses. Corresponding theoretical peaks are plotted with dotted lines. From right to left these spectra correspond to theoretical shell thicknesses of 14, 17, 24 and 30 nm. Experimental shell thicknesses determined by TEM were 20, 26, 29, 33 nm+/−4 nm.
Figure 4:
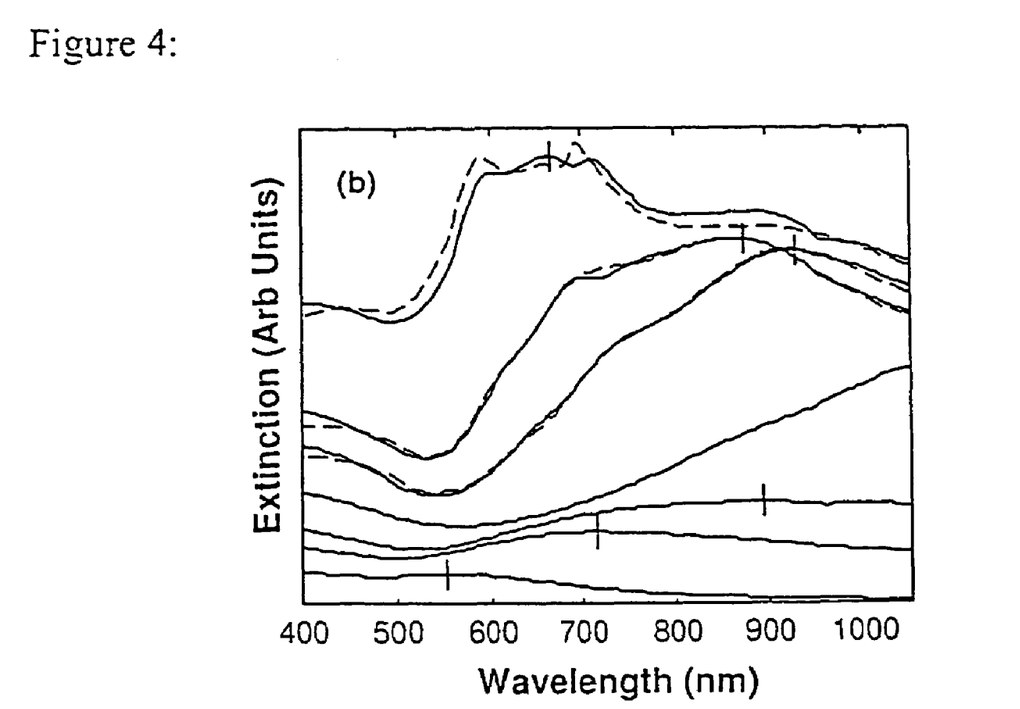
FIG. 4: Growth of gold shell on 340 nm diameter silica core particles. The dotted lines from right to left correspond to calculations with shell thicknesses of 17, 35, and 48 nm. TEM determined shell thicknesses were 18, 39, and 53 nm+/−12.

Before enlargement of the metal clusters, the metal clusters attached to the particles had the same UV-visible absorption spectrum as their natural colloidal form. As additional metal was deposited onto the clusters, the absorbance maximum of the particle shifted to longer wavelengths, as shown in the lower curves of FIGS. 3 and 4. When the gold shell was complete, the particles' absorbance maximum was related to its geometry, specifically, to the ratio of the thickness of the inner nonconducting layer to the thickness of the outer conducting layer. As the conducting layer crew thicker, the absorbance maximum of the particle shifted to shorter wavelengths, as shown in the upper curves of FIGS. 3 and 4. The progress of this reaction was followed spectrophotometrically and terminated when the desired wavelength for the absorbance maximum was obtained. Typically a color change occurred within 10 minutes. For 110 nm diameter core particles, typically a visible color chance is apparent, from faint brown to purple, blue, green, or yellow. Some of the other factors that influenced the optical absorption of the spectrum are the size of the core, the roughness of the shell, the shape of the core, additional reactants in solution that may be incorporated into the core during the reduction, the continuity of the shell, and the degree of aggregation of the particles.

Many different methods can be used to complete the metal shell once the nucleation sites are in place. One of skill in the art will realize that any method that can be used to develop a metal colloid into a larger metal colloid should be successful for the shell growth. For example, silver solutions such as the commercially available LI silver from Nanoprobes, Inc. may work. In addition, it is not necessary that the tethered seed particle be of the same material as the shell material. In one embodiment silver nitrate is reduced onto silica coated with UG. This is done in a basic solution with formaldehyde as a reductant and results in a silver shell. Photo-induced deposition of the metal shell onto the prepared nanoparticle surface is also possible.

Direct reduction of silver onto a non-conducting core can be accomplished with the reduction of silver directly onto a CdS semiconductor layer. In order to construct a CdS with a diameter greater than 20 nm it was necessary to first grow a CdS layer onto a silica core. This can be accomplished using water in oil microemulsions, for example. In one embodiment silver was reduced onto a silica/CdS particle by adding the particles to a solution of $AgNO_3$ and $NH_4$ and then slowly adding a $NH_3OHCl$ solution to develop the shell.

EXAMPLE VI

Nanoengineered Thermal Management Materials and Coatings

Figure 5:
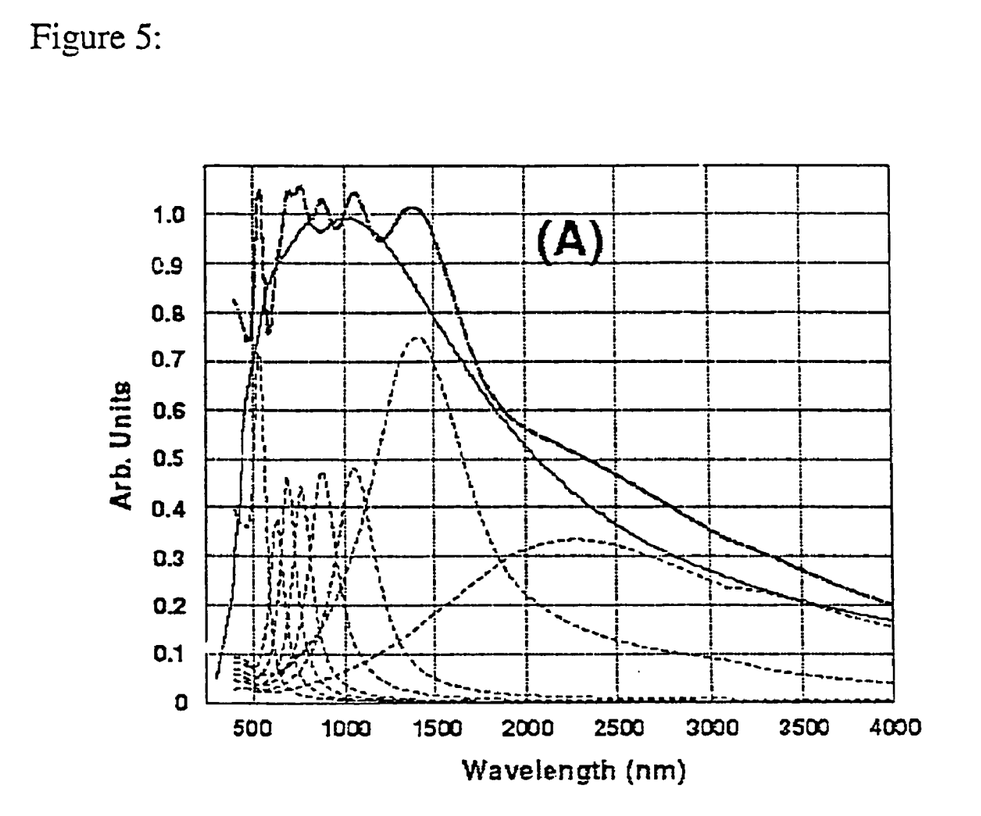
FIG. 5: Absorption spectrum of mixture of particles that would absorb or scatter all wavelengths of solar radiation available at the earth's surface.

The present application takes advantage of the fact that the sun's maximum radiant power that reaches the Earth's surface is distributed broadly across the visible and infrared regions of the electromagnetic spectrum and a mixture of nanoparticles can be developed to either absorb or scatter energy throughout that entire spectrum. The present technology is the only method known for systematic control of absorption or scattering of radiation across the entire range of the solar emission spectrum. In FIG. 5 is shown an example of a mixture of the present embodiments that can absorb the entire solar spectrum. In this Figure is shown the individual spectra of eight particles having varied core to shell ratios and that absorb distinct segments of the solar radiation spectrum. A mixture of these particles is capable of absorbing radiation across the entire solar spectrum.

Such a mixture can be incorporated into polymers, glasses, paints, epoxies, or other coating matrices by standard methods well known in the art. The thermal properties of these materials can then be used in appropriate applications that rely on absorption and scattering of solar energy or any source of electromagnetic radiation across the wavelength range of the mixture.

EXAMPLE VII

Nanoshell Windows

Figure 6:
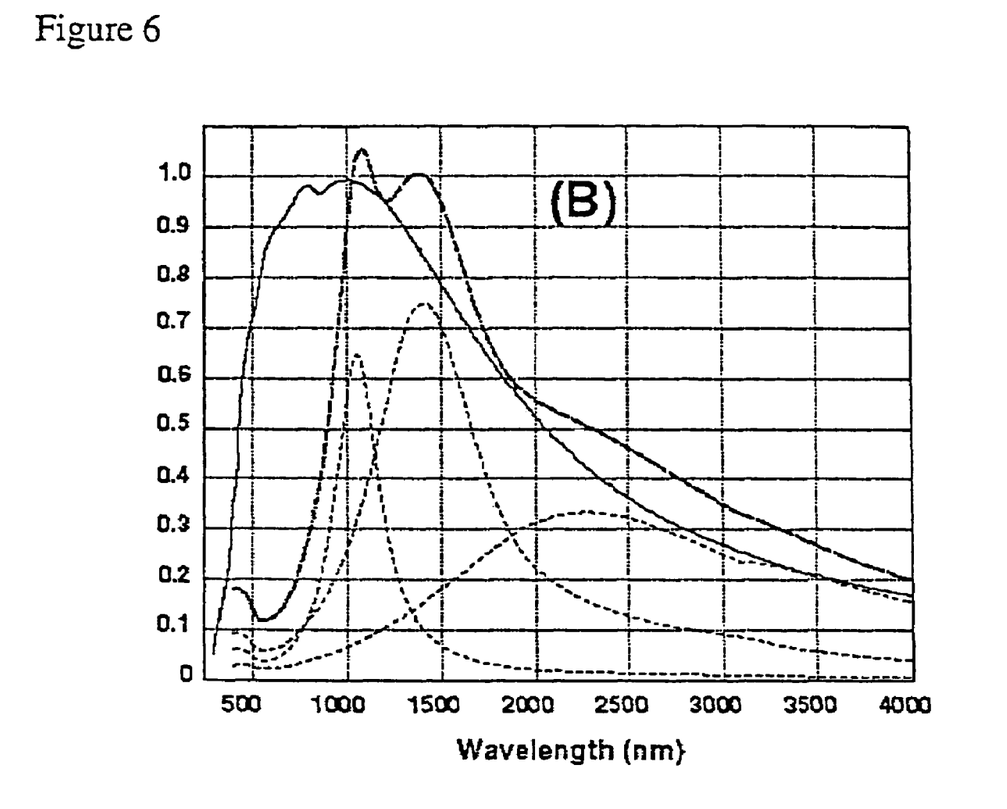
FIG. 6: Absorption spectrum of mixture of particles that would absorb or scatter only the infrared wavelengths of solar radiation available at the earth's surface.

In FIG. 6 is shown an example of a mixture of the present embodiments that can absorb the entire infrared region of the solar spectrum while allowing visible light from the sun to pass through. In this Figure is shown the individual and combined spectra of three distinct particles having varied core to shell ratios in a particle mixture and that absorb distinct segments of the solar radiation spectrum. These particles may be a subset of the mixture of Example VI.

Such a mixture can be incorporated into polymers, glasses, paints, epoxies, or other coating matrices by standard methods well known in the art. The thermal properties of these materials can then be used in appropriate applications that rely on trapping solar energy while at the same time allowing visible wavelengths to pass. Such materials could be incorporated into sunroofs and windows that would trap some fraction of incident radiation from a solar or nonsolar source while allowing a clear field of vision. Similarly incorporation of these particles into heat resistant paint would allow for the production of colored paints that have the ability to absorb or to scatter most of the sun's heat energy.

Similarly, it is possible to engineer "transmission windows" through which selected wavelengths of electromagnetic radiation can pass and incorporate those particles into similar materials. It is also possible to engineer materials that will strongly absorb or scatter over a specific wavelength range corresponding to the operating range of a laser or lasers, and be either translucent or transparent below and above the specific wavelength range. This type of material could be used for eye protection in the presence of a laser source or sources.

EXAMPLE VIII

Nanoengineered Solar Cells

Current solar energy cells only convert a small fraction of the sun's radiant energy into electrical energy. Clearly, converting absorbed radiation from across the entire solar spectrum into electricity would achieve higher solar cell efficiencies than is currently available. The present embodiment relies on the electron accepting capability of thin solid films of buckrninisterfullerene or $C_{60}$, a spherical carbon cage molecule. The photovoltaic effect of $C_{60}$ based thin film, which is enhanced by forming a heterojunction with a conducting polymer film, such as PPV, is sensitized to an enhanced photoresponse at longer wavelengths by introducing a layer of suitably designed metal nanoshells between the $C_{60}$ and the PPV. A dilute or dense layer of metal nanoshells is embedded at the interface between the conducting polymer and the $C_{60}$. The electrostatic field created by the heterojunction establishes an assymetric potential across the metal nanoshell layer. The strong electron donor-acceptor interaction between the metal-like conductor of the shell layer and the $C_{60}$ will cause the metal-like conductor of the shells to inject electrons into the $C_{60}$ layer when the shell layers are illuminated with radiation corresponding to their absorption resonance. The released electrons are detected as either a photocurrent or photovoltage by methods known in the art. Such a device could be made using spun polymer films, vacuum deposition, or other methods known to one skilled in the art. Any pair of electron donor-acceptor materials that could be sequentially deposited into such a layer structure could be used with metal nanoshells as photosensitive devices. This device may also consist of more than one layer of electron donor/metal nanoshell/electron acceptor layers.

It will be readily apparent to one skilled in the art that various substitutions and modifications may be made to the invention disclosed herein without departing from the scope and spirit of the invention. For example, the nanoparticle core used not be spherical and may retain other shapes such as planar sheets. Similarly, the invention may be employed to place metal nanoshells on planar sheets and other surfaces.

EXAMPLE IX

Optically Active Materials with Metal Nanoshell Dopants

The adjustable plasmon resonance of metal nanoshells can be used as dopants or additives to influence and modify the optical properties of optically active host materials, such as, but not limited to, conducting polymers or organic semiconductors. The nanoshell resonance can be designed to overlap with either the singlet or the triplet exciton resonances of the host material. Since metal nanoparticle resonances have excitation lifetimes of only a few picoseconds, any donor-acceptor interaction between the comparatively long-lived excitons of the conducting polymer and the nanoparticles will result in strong quenching of the specific excitation or excitations of the host material to which the nanoshell resonance has been tuned. This provides a method for strongly modifying the optical properties of a material with little modification of its chemical properties.

EXAMPLE X

Optically Active Species Inside Metal Nanoshell Nanocavities

A straightforward variation of the fabrication method outlined above enables the insertion of optical absorbers and luminescent species into the dielectric cores of metal nanoshells. Procedures for bonding functionalized dye molecules into silica nanoparticles grown by the Stober method have been demonstrated by van Blaaderen and Vrij, incorporated herein by reference to the extent it discloses such methods. Introducing an optically absorbing species into the core will strongly influence the plasmon resonance shift and width. Conversely, the optical field enhancement within the metal "nanocavity" modifies the absorption and fluorescent properties of the chromophores incorporated within this nanostructure.

EXAMPLE XI

Metal Nanoshell Structures Via Planar Fabrication Methods

There also exists the possibility of fabricating spherical, hemispherical, or other types of geometries directly from planar semiconductor or dielectric surfaces. For example, on silicon substrates specific chemical etching techniques result in well-defined nanoscale structures extending up from the surface of the substrate. Using the unique methods described herein, such nanostructures can be metal-coated, resulting in devices or regions of devices with unique properties. For example, an array of nanometer-sized hemispheres etched onto a silicon substrate could be coated with a thin layer of gold. Such a substrate would have the same optical tunability as nanoshells, that is, the optical absorption of the substrate would have a resonance defined by the size of the hemispheres and the thickness of the metal layer. Such substrates would be useful as SERS-based chemical sensors. Similarly, nanoshells attached or directly formed onto small cantilevers, such as those used in scanning force microscopy, could be used as small localized probes for the wavelength-specific detection of radiation: in this embodiment, the deflection or the vibrational frequency of the cantilever may be monitored with either response 5 being proportional to the absorbed energy content of the nanoshell or nanoshells attached or fabricated onto the cantilever structure. Such microbolometers would find applications in a variety of diagnostic environments requiring localized optical detection, or optical detection by a very small (micron-sized) structure.

REFERENCES CITED

Meyer H. Bimboim and Arthur K. Noeves, U.S. Pat. No. 5,023,139 issued Jun. 11, 1991; Nonlinear Optical Materials.

Daniel G. Duff, Alfons Baiker, Ian Gameson, and Peter P. Edwards (1993) Langmuir 9, 2310-2317. A New Hydrosol of Gold Clusters. 2. A Comparison of Some Different Measurement Techniques.

Jovan Nedeljkovic and Ramesh C. Patel (1991) Appl. Phys. Lett. 58, 2461-2463. Observation of Plasmon-Enhanced Optical Extinction in Silver-Coated Silver Bromide Nanoparticles.

M. J. Puska and R. M. Nieminen, (1993) Physical Review A 47, 1181-1186. Photoabsorption of atoms inside C60.

Werner Stober, Arthur Fink, and Ernst Bohn, (1968) J. Colloid and Interface Science 26, 62-69. Controlled Growth of Monodisperse Silica Spheres in the Micron Size Range.

H. S. Zhou, I. Honma, and H. Komiyama, and J. W. Haus, (1994) Phys. Rev., 50, 12,052-12,056. Controlled Synthesis and Quantum-Size Effect in Gold-Coated Nanoparticles.

R. D. Averitt, D. Sarkar, and N.J. Halas, (1997) Phys. Rev. Lett. 78, 4217-4220. Plasmon Resonance Shifts of Au-Coated Au2S Nanoshells: Insight into Multicomponent Nanoparticle Growth.

K. V. Sarathy, G. Raina, R. T. Yadav, G. U. Kulkarni, and C. N. R. Rao, (1997), J. Phys. Chem. B., 101, 9876-9880. Thiol-Derivatized Nanocrystalline Arrays of Gold, Silver, and Platinum.

U. Kreibig, M. Gartz, and A. Hilger, (1997), Berichte der Bunsen-Gesellchaft fur Physikalische Chemie, 101, 1593-1603. Mie Resonances: Sensors for Physical and Chemical Cluster Interface Properties.

A. van Blaaderen and A. Vrij, (1992), Langmuir, 8, 2921-2925. Synthesis and characterization of colloidal dispersions of fluorescent, monodisperse silica spheres.

What is claimed is:

1. A nanoparticle comprising:
   at least one non-conducting inner layer;
   at least one conducting shell layer surrounding the inner layer, the thickness of said shell layer being independent of the radius of said inner layer and less than the bulk electron mean free path of the material comprising the shell layer.

2. The nanoparticle of claim 1 wherein the shell comprises a metal or metal alloy.

3. The particle of claim 2, wherein a wavelength absorbance maximum is between 740 nm and 5 μm.

4. The nanoparticle of claim 1 wherein said conducting shell layer comprises an organic conducting material.

5. The nanoparticle of claim 1 wherein said nanoparticle comprises at least one additional non-conducting layer in an alternating sequence with at least one conducting shell layer.

6. The nanoparticle of claim 1 wherein said non-conducting inner layer comprises a dielectric material selected from the group consisting of silicon dioxide, titanium dioxide, PMMA, polystyrene, dendrimers, and combinations thereof.

7. The nanoparticle of claim 1 wherein said non-conducting inner layer comprises a semi-conducting material.

8. The nanoparticle of claim 1 wherein said non-conducting inner layer comprises an organic molecule or an organic superinolecular structure.

9. The nanoparticle of claim 1 wherein said non-conducting inner layer comprises a mixture of non-conducting materials.

10. The nanoparticle of claim 1 wherein said non-conducting inner layer comprises an optically absorbing material.

11. The nanoparticle of claim 1 wherein said non-conducting inner layer comprises a fluorescent material.

12. The nanoparticle of claim 1 further comprising a conducting layer sandwiched between two non-conducting layers.

13. The nanoparticle of claim 2 wherein said shell comprises a metal selected from the group consisting of coinage metals, noble metals, transition metals, and synthetic metals.

14. The nanoparticle of claim 1 wherein said non-conducting inner layer comprises a dielectric material.

15. A composition comprising a plurality of nanoparticles according to claim 1 wherein the diameter of said nanoparticles varies by less than 100%.

16. The nanoparticle of claim 1 wherein said conducting shell layer coats at least 30% of said non-conducting inner layer.

17. The nanoparticle of claim 16 wherein said conducting shell layer coats at least 30% but less than 100% of said non-conducting inner layer.

18. The nanoparticle of claim 1 wherein said conducting shell layer completely surrounds said non-conducting inner layer.

19. The nanoparticle of claim 1 wherein said conducting shell layer is linked to said non-conducting core layer by a linker molecule.

20. The nanoparticle of claim 1 wherein said nanoparticle is approximately spherical.

21. The nanoparticle of claim 1 wherein said nanoparticle is non-spherical.

22. The nanoparticle of claim 21 wherein said nanoparticle is cubical, cylindrical or hemispherical.

23. A Raman sensing device comprising the nanoparticle of claim 1.

24. The device of claim 23 wherein an electromagnetic excitation of the device is in the near-infrared.

25. The particle of claim 1 wherein a wavelength extinction maximum is between 400 nm and 20 μm.

26. The particle of claim 25, wherein a wavelength absorbance maximum is between 740 nm and 5 μm.

27. A light detecting device comprising the nanoparticle of claim 1.

28. A chemical sensing device comprising the nanoparticle of claim 1.

29. A bolometer comprising the nanoparticle of claim 1.

30. A microbolometer comprising the nanoparticle of claim 1.

31. A sensing cantilever device comprising the nanoparticle of claim 1.

32. A dopant in an optically active material comprising the nanoparticle of claim 1.

33. A polymer comprising the nanoparticle of claim 1.

34. A photovoltaic solar cell comprising the nanoparticle of claim 1.

35. An infrared detector comprising the nanoparticle of claim 1.

36. An infrared absorbing device comprising the nanoparticle of claim 1.

37. A nanoparticle comprising
   at least one inner layer;
   at least one shell layer surrounding said inner layer,
   wherein the dielectric constant of said shell layer is less than that of the inner layer and the thickness of said shell layer is independent of the radius of said inner layer and less than the bulk electron mean free path of the material comprising the shell layer.

38. The nanoparticle of claim 37 wherein the shell comprises a metal.

39. The nanoparticle of claim 38 wherein said shell layer comprises a metal selected from the group consisting of coinage metals, noble metals, transition metals, and synthetic metals.

40. The nanoparticle of claim 37 wherein said shell layer comprises an organic conducting material.

41. The nanoparticle of claim 37 wherein the shell comprises a metal alloy.

42. A composition comprising a plurality of nanoparticles according to claim 37 wherein the diameter of said nanoparticles varies by less than 100%.

43. The nanoparticle of claim 37 wherein said conducting shell layer coats at least 10% of said non-conducting inner layer.

44. The nanoparticle of claim 43 wherein said conducting shell layer coats at least 10% but less than 100% of said non-conducting inner layer.

45. The nanoparticle of claim 37 wherein said conducting shell layer completely surrounds said inner layer.

46. The nanoparticle of claim 37 wherein said conducting shell layer is linked to said non-conducting core layer by a linker molecule.

47. The nanoparticle of claim 37 wherein said nanoparticle is approximately spherical.

48. The nanoparticle of claim 37 wherein said nanoparticle is non-spherical.

49. The nanoparticle of claim 48 wherein said nanoparticle is cubical, cylindrical or hemispherical.

50. A light detecting device comprising the nanoparticle of claim 37.

51. A chemical sensing device comprising the nanoparticle of claim 37.

52. A bolometer comprising the nanoparticle of claim 37.

53. A microbolometer comprising the nanoparticle of claim 37.

54. A sensing cantilever device comprising the nanoparticle of claim 37.

55. A dopant in an optically active material comprising the nanoparticle of claim 37.

56. A polymer comprising the nanoparticle of claim 37.

57. A photovoltaic solar cell comprising the nanoparticle of claim 37.

58. An infrared detector comprising the nanoparticle of claim 37.

59. An infrared absorbing device comprising the nanoparticle of claim 22.

60. A Raman sensing device comprising the nanoparticle of claim 37.

61. The device of claim 45 wherein an electromagnetic excitation of the device is in the near-infrared.

62. The particle of claim 37 wherein a wavelength extinction maximum is between 400 nm and 20 μm.

* * * * *

UNITED STATES PATENT AND TRADEMARK OFFICE
CERTIFICATE OF CORRECTION

| | | |
|---|---|---|
| PATENT NO. | : 7,371,457 B2 | Page 1 of 1 |
| APPLICATION NO. | : 10/752181 | |
| DATED | : May 13, 2008 | |
| INVENTOR(S) | : Steven J. Oldenburg et al. | |

It is certified that error appears in the above-identified patent and that said Letters Patent is hereby corrected as shown below:

On the face of the patent, Item (73) Assignee: Replace "William Marsh Rich University" with -- William Marsh Rice University --

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,371,457 B2 Page 1 of 1
APPLICATION NO. : 10/752181
DATED : May 13, 2008
INVENTOR(S) : Steven J. Oldenburg et al.

It is certified that error appears in the above-identified patent and that said Letters Patent is hereby corrected as shown below:

Column 1, Lines 21-23, replace "The research that resulted in this invention was funded by the Office of Naval Research, N00014-97-1-0217, and the National Science Foundation, ECS-9258118." with -- This invention was made with government support under Grant Number N00014-97-1-0217 awarded by the Office of Naval Research, and Grant Number ECS-9258118 awarded by the National Science Foundation. The government has certain rights in the invention. --

Signed and Sealed this

Twenty-second Day of June, 2010

David J. Kappos
*Director of the United States Patent and Trademark Office*